United States Patent [19]

Moyer et al.

[11] Patent Number: 5,212,057
[45] Date of Patent: May 18, 1993

[54] BIOLOGICAL SYSTEM FOR CONSTRUCTING AND TESTING VIRAL VACCINES

[75] Inventors: Richard W. Moyer; David C. Bloom, both of Gainesville, Fla.

[73] Assignee: University of Florida, Gainesville, Fla.

[21] Appl. No.: 455,483

[22] Filed: Dec. 22, 1989

Related U.S. Application Data

[63] Continuation-in-part of Ser. No. 262,769, Oct. 26, 1988, abandoned.

[51] Int. Cl.$^5$ .................. C12Q 1/70; C12N 15/00
[52] U.S. Cl. .................... 435/5; 435/235.1; 435/236; 435/320.1; 435/238
[58] Field of Search ............ 435/5, 6, 235, 236, 435/320, 238, 172.1, 172.3; 935/32, 57, 56, 76, 77, 79; 424/9

[56] References Cited

U.S. PATENT DOCUMENTS 4,769,330 9/1988 Paoletti et al. .................. 435/172.3

OTHER PUBLICATIONS

Panicali et al., *Proc. Natl. Acad. Sci. U.S.A.*, vol. 80, pp. 5364–5368, Sep. 1983, "Construction of Live Vaccines by Using Genetically Engineered Poxviruses: Biological Activity of Recombinant Vaccinia Virus Expressing Influenza Virus Hemagglutinin."

Rodriguez et al., *J. Virol.*, vol. 61, No. 11, Nov. 1987, pp. 3550–3554, "Mapping and Nucleotide Sequence of the Vaccinia Virus Gene that Encodes a 14-Kilodalton Fusion Protein".

Piccini, A., and E. Paoletti (1986) "The use of vaccinia virus for the construction of recombinant vaccines," Bioessays 5:248–252.

Brown, F., G. C. Schild, and G. L. Ada (1986) "Recombinant vaccinia viruses as vaccines," Nature 319:549–550.

*Primary Examiner*—Robert J. Hill, Jr.
*Assistant Examiner*—Laurie Scheiner
*Attorney, Agent, or Firm*—Saliwanchik & Saliwanchik

[57] ABSTRACT

Disclosed is a novel biological system for 1) the evaluation of potential complications of live virus vaccines prior to actual testing in animals or in the field, and 2) the construction of vaccine vectors in which the ability to grow within specific organs or tissues has selectively been eliminated from the virus.

**2 Cla

Figure 1

NULL VECTOR RATIONALE

| RPuhr23 parent | RPuhr23 construct strain | RPuhr23 tester virus |
|---|---|---|
| 1) HA gene non-functional | 1) HA gene reconstructed | 1) HA gene inactivated when used as cloning site |
| 2) Avirulent | 2) Avirulent | 2) Virulence depends on viral genes inserted |
| 3) 30 kb of viral genome deleted | 3) 30 kb of viral genome deleted | 3) < 30 kb deleted, depending on size of fragments added back |
| 4) Host range restricted<br>a) human (-)<br>b) rat (-)<br>c) rabbit (-)<br>d) pig (-)<br>e) avian (+) | 4) Host range restricted<br>a) human (-)<br>b) rat (-)<br>c) rabbit (-)<br>d) pig (-)<br>e) avian (+) | 4) Host ranges and virulence to be tested |

Figure 2
APPLICATION OF THE NULL VECTOR SYSTEM STRATEGY

RPµhr23 avirulent HA negative strain — Non-functional HA Gene — HA−  (Hemadsorption Assay Plates)

+

Plasmid pHGN1 contains a functional HA gene

Transfection/recombination ↓ HA gene reconstructed

RPµhr23 avirulent HA positive strain — Recombinant RPµhr23 with functional HA — HA+

+

Shuttle plasmid pHGN3 with a segment of the deleted region of the RPV genome inserted.

Transfection/recombination ↓ HA gene inactivated

RPµhr23 HA negative new viral DNA sequences inserted — Insertion of the DNA interrupts the hemagglutinin gene restoring the RPµhr 23 to its original HA− (null) phenotype. — HA−

Isolation of the Vaccinia Hemagglutinin Gene from Vaccinia Strain IHD-J

Figure 3

BIOLOGICAL SYSTEM FOR CONSTRUCTING AND TESTING VIRAL VACCINES

The subject invention was developed, in part, with funds from NIH grant Al 15722.

CROSS-REFERENCE TO A RELATED APPLICATION

This application is a continuation-in-part of our co-pending application Ser. No. 262,769, filed Oct. 26, 1988, now abandoned.

BACKGROUND OF THE INVENTION

Post-vaccinial encephalitis and disseminated vaccinia are major concerns with the use of vaccinia virus recombinants as immunization vectors in man. However, because of the efficacy of vaccinia virus recombinants, this virus is still being evaluated in a number of laboratories as a potential live vaccine vector against a wide variety of both human and animal pathogens. Its potential as a vaccine is evident because of its successful employment in the worldwide eradication of Smallpox. Since that time, there have been published a number of studies demonstrating the suitability of the virus as a vector for the delivery and expression of foreign antigens. Since these foreign antigens behave as would a gene of the vaccinia vector itself, a significant immune response and subsequent protection against the antigen, and therefore the infectious agent of interest, would occur simultaneously with the mounting of an immune response against the vaccinia virus vector itself (Piccini, A., and E. Paoletti [1986] "The use of vaccinia virus for the construction of recombinant vaccines," Bioessays, 5:248,252.). Based on past experience, there are questions concerning both the safety and the occasional complications (such as spreading and growth in the brain and nervous system) that can arise from the use of vaccinia as a vaccine. Therefore, if vaccinia virus is to be widely used as a vaccine vector for wide scale human or animal use, efforts to design attenuated strains of virus exhibiting a lesser degree of intrinsic virulence must be undertaken (Brown, F., G. C. Schild, and G. L. Ada [1986] "Recombinant vaccinia viruses as vaccines," Nature 319:549-550).

Over the past 4 or 5 years, there has been a tremendous interest in the possibility of live vaccine vectors and the specific use of vaccinia virus. Vaccinia virus is a known entity, and has received endorsement from the World Health Organization (WHO) for this purpose. One overwhelming reason for this endorsement is the fact that the "cold chain" can be broken. Vaccinia based vaccines do not require refrigeration and can be administered in the field by non-skilled personnel. The market is world-wide, and the technology described here is suitable for both human and animal vaccines.

The commercial possibilities are enormous. The use of vaccinia virus based vaccine technology is appropriate for both human and animal vaccines. Each vaccine construct will have to undergo rigorous testing before endorsement and thereafter periodic testing during production. A simple test system which allows both predictions as to relative virulence coupled with the possibility of custom designing each and every vaccine would facilitate the overall process tremendously and fill a niche in the field which is currently overlooked. The invention described herein accomplishes these highly desirable goals.

BRIEF SUMMARY OF THE INVENTION

The subject invention concerns a novel vector system for the assay of tissue tropism and virulence potential of viral vaccines. Specifically, the invention comprises a biological system for (1) the evaluation of potential complications of live virus vaccines prior to actual testing in animals or in the field, and (2) the construction of vaccine vectors in which the ability to grow within specific organs or tissues has selectively been eliminated from the virus.

The invention vector system is exemplified herein by use of vaccinia/rabbit poxvirus. This vector system, referred to as the "null vector system," is shown in FIG. 1 with reference to rabbit poxvirus. This figure shows that the null vector system is comprised of the components:

1. A live rabbit poxvirus deletion mutant, lacking some 30 kilobases of DNA. This deletion mutant is derived not from vaccinia, but from the closely related rabbit poxvirus, and it is severely attenuated. No growth of this virus can be detected within any tissue or organ (including the brain) within the animal body except the outer epidermal tissue of the skin. In addition, this mutant exhibits a drastically reduced host range in vitro and fails to grow on many cell lines normally permissive for the wild type virus.
2. A shuttle plasmid, constructed to allow for the efficient, selective introduction of foreign DNA into the deletion mutant.
3. A tissue culture assay system for growth of the virus in vitro that comprises marker cell lines that have been correlated with the ability of the virus to grow within specific tissues and organs within the body.
4. Not shown in FIG. 1 is an in vivo assay system monitoring the weight loss response of test animals, e.g., mice, to recombinant virus. The preferred route of administration to the test animal is intracranial injection.

These components allow for the insertion of DNA into the avirulent deletion mutant and an interpretation of the effect of the newly inserted, expressed foreign DNA on in vivo virulence of the construct by the simple test of growth either on the predictive cell lines, or by administration to animals. The essential feature of the system, as exemplified herein, involves the novel use of the hemagglutinin gene derived from vaccinia virus which has been isolated and cloned into the rabbit poxvirus genome. Rabbit poxvirus does not synthesize an active hemagglutinin. The cloning of foreign DNA into the hemagglutinin gene is accomplished by making use of the shuttle plasmid (FIG. 2) which also contains the hemagglutinin gene interrupted by a multicloning site which allows for simple insertion of the DNA sequences to be tested. The shuttle plasmid has been designed so that successful insertion of the foreign DNA into rabbit poxvirus tested strain renders the cloned hemagglutinin gene of the virus inactive.

Further, the subject invention also concerns the novel diagnostic use of known cells and a sensitive weight loss animal model to asses the effects and to act as indicators of potential biological complication with viral vaccines. Still further, the invention concerns the use of avirulent poxviruses as a vaccine, and as novel vaccine vectors.

BRIEF DESCRIPTION OF THE DRAWINGS

FIG. 1 depicts the rationale for the null vector system.

FIG. 2 shows the application of the null vector system strategy.

FIG. 3 depicts isolation of the vaccinia hemagglutinin gene from vaccinia strain IHD-J.

DETAILED DESCRIPTION OF THE INVENTION

Figure 4:
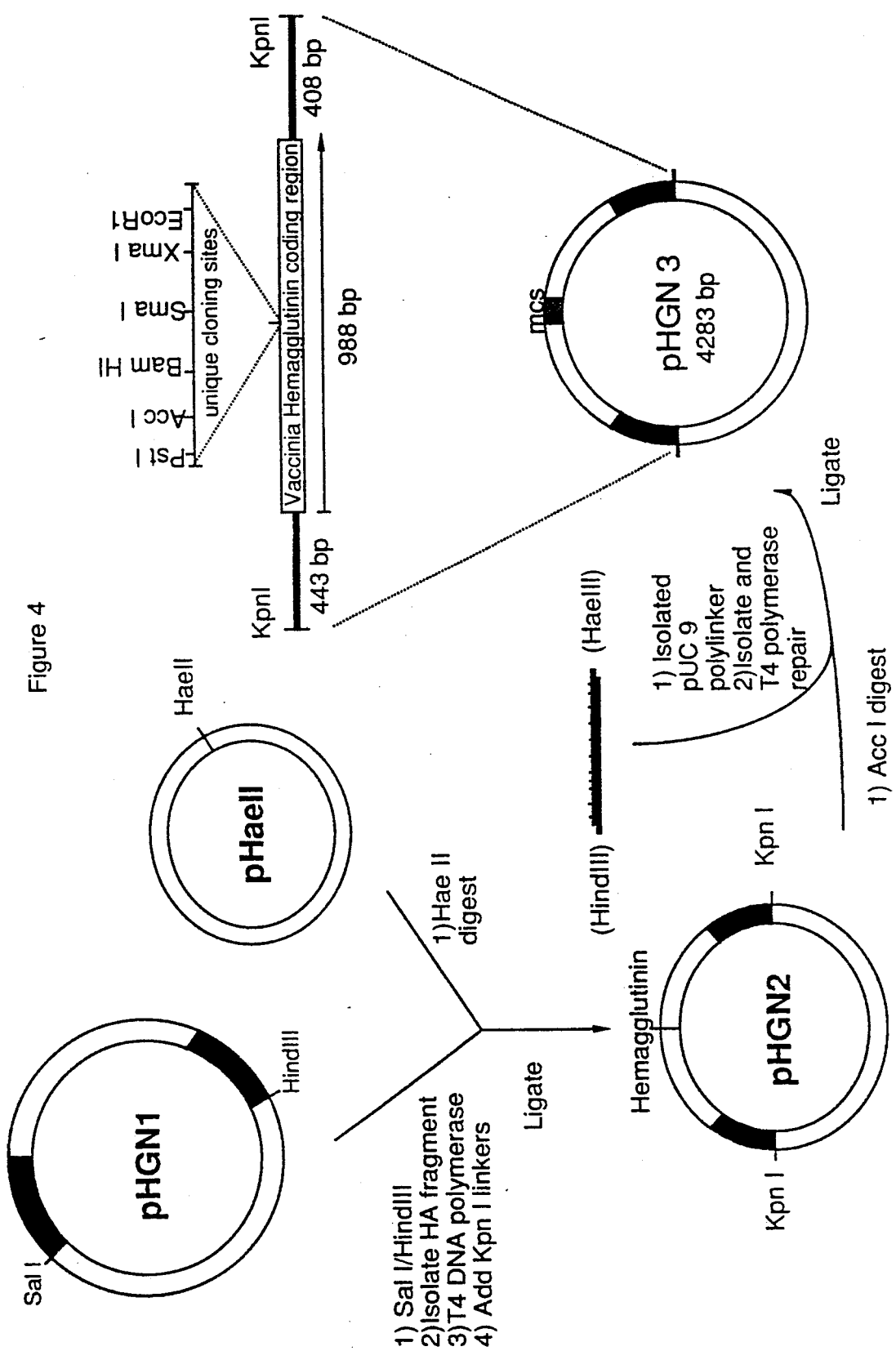
FIG. 4 shows construction of hemagglutinin insertion vector.

We have invented a novel vector system which provides a predictive index concerning relative virulence and the ability of a given vaccine strain to grow within specific tissues (such as the brain) within the body. The system also opens up the way for the design of vaccine strains of known and specifically engineered tissue and organ tropism.

The salient feature of the system, as disclosed herein, is that we have engineered a "new gene" into rabbit poxvirus solely for use as a cloning site. In wild-type or control strains, this gene, e.g., the hemagglutinin gene, is not expressed. Therefore, by using this gene as a cloning site, insertion of foreign DNA inactivates the hemagglutinin gene so that any altered effects of growth or pathogenicity can only result from the newly inserted foreign DNA. In addition, the use of the hemagglutinin gene provides a simple colorimetric assay for potential recombinants since hemagglutinin positive (HA+) plaques of virus absorb red blood cells whereas hemagglutinin negative (HA−) plaques of virus do not.

Due to the extremely close relatedness of rabbit poxvirus and vaccinia, this system allows for the identification of genetic elements responsible for specific tissue tropism and virulence of either virus. Localization of these virulence and tissue tropic associated genes involves the systematic reintroduction of sequences deleted in an avirulent tester strain, e.g., RPV$\mu$hr23, and then an assay of the resulting recombinants for changes in growth or pathogenicity in the test system. Once these genes have been localized, they can be selectively eliminated from any vaccine strain, if desired. Likewise, this system can be used to detect any unanticipated alterations in growth of any newly-designed vaccine construct, thus greatly aiding in the development of new recombinant vaccines. This system also can be routinely used for "batch analysis" of production vaccines, thus providing a quick and cost-efficient method to insure that vaccine lots are uniform, and predictably avirulent, based simply on the ability to grow on well-defined indicator cell lines.

Any avirulent member of the poxvirus family can be used so long as it is capable of sufficient expression of an immunogen to sensitize the host. Thus, the avirulent poxvirus can be a deletion mutant capable of growth.

The poxvirus can be modified, in accord with the invention, by inserting a suitable marker gene, e.g., the hemagglutinin gene derived from vaccinia virus. Though the hemagglutinin gene is disclosed herein to exemplify the invention, any prokaryotic or eukaryotic gene whose expression and subsequent inactivation which could be selected for can be used. For example, the bacterial gene encoding luciferase or $\beta$-galactosidase can be used. The modification of the poxvirus can be conducted using standard procedures well known in the art, and as shown in FIG. 2 of the drawings. General techniques to produce modified virus are disclosed in U.S. Pat. No. 4,603,112 (Paoletti et al.).

As shown in FIG. 2, the shuttle vector (plasmid) containing the gene of interest (and the marker or indicator gene), flanked by suitable poxvirus sequences, will undergo recombination with poxvirus which results in the integration of the flanked genes into the poxvirus genome. This recombination occurs in a eukaryotic host cell. The cells are initially infected with a poxvirus and then transfected with the DNA vector. Infection of eukaryotic cells is by standard well-known procedures. Following infection and transfection, the cells are incubated under standard conditions to allow for virus replication at which time in vivo recombination occurs between the homologous poxvirus sequences in the shuttle vector and the poxvirus sequences in the genome.

Selection of recombinant viral progeny can be done by standard procedures well known in the art, as disclosed previously. For example, if the hemagglutinin gene is used as the marker gene, a simple colorimetric assay can be employed to identify the presence of successful recombinants. Another marker or indicator gene which can be used in the E. coli lacZ gene encoding $\beta$-galactosidase. Recombinant viruses expressing $\beta$-galactosidase can be selected for by using a chromogenic substrate for the enzyme.

Vaccines comprising live recombinant viruses expressing immunogenic proteins, e.g., rabies virus glycoprotein, herpes simplex virus type 1 glycoprotein B, and Epstein-Barr virus glycoprotein gp340, can be used to vaccinate humans and animals (See Moss, B. and C. Flexner [1987] "Vaccinia virus expression vector," Ann. Rev. Immunol. 5:305-324). Such vaccines can be administered intradermally, as was done for smallpox vaccination. Other routes of administration can be used, if desired, depending on the protection sought for any particular disease.

Following are examples which illustrate procedures, including the best mode, for practicing the invention. These examples should not be construed as limiting. All percentages are by weight and all solvent mixture proportions are by volume unless otherwise noted.

EXAMPLE 1

Construction of RPµhr23 HA+ Recipient Strain

RPµhr23 is a well-known, spontaneously occurring white pock mutant of wild-type rabbitpox virus (Utrecht strain) that resulted from the passage of wild-type virus on the chorioallantoic membrane of a chicken egg. This isolate was first described by Fenner and Sambrook (Fenner, F. and J. F. Sambrook [1966] Virology 28:600–609).

Since RPµhr23 does not have a functional hemagglutinin gene, RPµhr23 HA+ was constructed by introducing a functional hemagglutinin gene into the RPµhr23 (HA−) parental strain. This construction involved two steps: 1) isolating a functional HA gene from the known vaccinia virus strain IHD-J (HA+) and 2) introducing it into the RPµhr23 (HA−) by homologous recombination to form the RPµhr23 (HA+) recepient strain. The steps involved in the construction are outlined below.

1. Isolation of the vaccinia IHD-J hemagglutinin gene

Vaccinia IHD-J was obtained from the American Type Culture Collection (ATCC VR-156). This strain of vaccinia was chosen as the source for the hemagglutinin gene because this gene had been previously mapped and sequenced (Shida, H. [1986] Virology 150:451–462), thus facilitating genetic manipulation and its use as an insertional vector. The hemagglutinin gene was subcloned from vaccinia (see FIG. 3) by digesting the purified vaccinia DNA with the restriction endonucleases HindIII and EcoRI (New England Biolabs). The resulting fragments of this double digest were resolved by electrophoresis on a 0.5% agarose gel in Tris-Borate buffer (TBE; 89 mM Tris base, 89 mM Boric acid, 30M Na$_2$EDTA; pH 8.3) at 50 V for 2 hr. The 7.8 kb fragment containing the hemagglutinin gene was easily resolved, and excised. The DNA was electroeluted using the IBI electroelutor. This fragment can be subcloned into pUC 9 (Pharmacia, Inc.) and transformed into bacterial strain E. coli UT481. Other strains such as E. coli DH5α(BRL) can be used. The resulting plasmid which contained the EcoRI/HindIII fragment containing the functional hemagglutinin gene was designated pHGN. In order to minimize the amount of extraneous viral sequences flanking the hemagglutinin gene, pHGN was digested with the restriction endonucleases HindIII and SalI which excise a 1800 bp fragment with contains the vaccinia hemagglutinin gene and approximately 400 bp of viral flanking sequence on either side of the coding region for the hemagglutinin gene product. This 1800 bp fragment was excised from the gel and electroeluted as described previously. The resulting DNA was then treated with T4 DNA polymerase (International Biotechnologies) in order to produce flush ends. Synthetic KpnI linkers were then added, and ligated to the fragment. The resulting mixture was then subjected to digestion with KpnI restriction endonuclease, and the cut linkers purified away through a Sephadex G-50 spun column. The resulting 1806 bp fragment, which consisted of the isolated hemagglutinin fragment and the KpnI linkers on each end, was ligated to pUC 9 which had been digested with KpnI. The ligated mixture was then used to transform E. coli UT481, and the resulting recombinant was designated pHGN1. The important features of this plasmid is that if contained the 988 bp hemagglutinin gene, and a total of 853 bp of flanking sequence, approximately 400 on each end. The gene was cloned into pUC 9 using KpnI linkers to aid in excising the gene for future manipulation. The flanking sequence allowed the hemagglutinin to recombine into rabbit poxvirus.

2. Transfection of PRµhr23 (HA−) with pHGN1 to yield RPµhr23 (HA+) recipient strain.

The parental strain of RPµhr23 (HA−) was transfected with the pHGN1 plasmid by a modification of a commonly used procedure (Condit, R. C., A. Motyczka, and G. Spizz [1983] Virology 128:429–443). Primary chicken embryo fibroblasts (CEF) were grown in medium 199 (Gibco) supplemented with 10% fetal bovine serum, 3 mg/ml tryptose phosphate broth, 2 mM glutamine, 100 units penicillin, 100 mg streptomycin, and 0.1 mg pyruvate per ml. For the transfection, media was aspirated from a confluent monolayer of primary chicken embryo fibroblasts, and was washed twice with phosphate-buffered saline (PBS; 0.01M sodium phosphate plus 0.15M NaCl [pH7.2]), and infected with RPµhr23 (HA−) at a multiplicity of infection (m.o.i.) of 0.05 in unsupplemented media. The virus was allowed to adsorb for two hr by incubating at 37° C., 5% CO$_2$ with humidity. During this incubation, 40 µg of pHGN1 plasmid DNA was diluted with 1×HEPES Buffered Saline (20 mM HEPES, 150 mM NaCl, 700M Na$_2$HPO$_4$, 5 mM KCl, 6 mM Glucose) to a final volume of 4 ml. A pasteur pipet was then used to cavitate the DNA solution while 1/20 volume (200 µl) of 2.5M CaCl$_2$ was added. This mixture was then allowed to precipitate at room temperature for 1 hour. At the appropriate time, the infecting inoculum was removed from the CEF monolayer, and the cells washed two times with unsupplemented medium. 4 ml of the precipitated DNA was then added to the monolayer and incubated for 30 min at room temperature. After this incubation, 40 ml of supplemented media was added to the monolayer and incubated 3.5 hr at 37° C. After this time period, the media was aspirated, and fresh media added. The monolayer was then incubated for 48 hr at 37° C. The infected cells were then harvested by scraping with a rubber policeman, and concentrated by centrifugation at 8000×g for 20 min. The infected cell pellet was resuspended in 10 ml PBS and briefly sonicated with a probe sonicator to disrupt the cells and release the virus. In order to identify the HA+ recombinant, the transfection mixture was plaqued on QT-6 quail cells at medium density, overlayed with complete medium containing 1% methylcellulose, and grown for 2 days. The HA+ recombinants were visualized using a hemabsorption assay. Briefly, the methylcellulose was aspirated from the dishes, and the monolayers washed 3 times with PBS to remove the residual methylcellulose. 15 ml of a 0.5% suspension of washed chicken red blood cells were added to the monolayer, and the monolayer incubated at 37° C. for 15 min. The red blood cell suspension was then removed, and the HA+ plaques could be seen by their red color. Several of these plaques were picked and purified by three rounds of plaque purification.

EXAMPLE 2

Construction of the Insertion Plasmid pHGN3

In order to facilitate the insertion of cloned DNA into the hemagglutinin gene of RPμhr23 (HA+), plasmid pHGN1 was modified by the removal of extraneous pUC sequences, and the addition of a multicloning site which generates 6 unique restriction sites within the HA gene. This allows greater flexibility in cloning DNA into this gene. The construction of this plasmid is shown in FIG. 4 and outlined below.

1. Removal of the lac Z from pUC

The first step of the construction involved the removal of the lacZ gene and internal polylinker from pUC 9. pUC 9 was digested with the restriction endonuclease HaeII, which liberates two fragments, one of which contains the lacZ cassette and polylinker, and the other which contains sequence essential for the replication of the plasmid. This restriction digest was ligated, transformed into *E. coli*, and β-galactosidase negative bacteria were selected by the addition of X-gal and IPTG to the selection medium. This plasmid was isolated and shown to lack the lacZ cassette fragment. The 1800 bp hemagglutinin gene was isolated from pHGN1, and ligated into this modified pUC plasmid by the addition of KpnI linkers to the plasmid. The resulting plasmid was designated pHGN2.

2. Insertion of the multicloning site

The multicloning site was obtained by digesting pUC 9 with the restriction endonucleases HindIII and HaeIII, and isolating the resulting 47 bp multicloning site by electrophoresis on a 4% Nusieve gel (FMC Bioproducts). The fragment was electroeluted from the agar and treated with T4 DNA polymerase to produce blunt ends. The fragment was then inserted into pHGN2 that had been digested with the endonuclease AccI, which cleaves at base 43 of the 5' coding region of the hemagglutinin gene. The resulting plasmid was designated pHGN3, and allows one to easily clone DNA fragments into the hemagglutinin gene, which then acts as a shuttle to introduce them into the RPμhr23 vector.

EXAMPLE 3

Assay of RPμhr23 Recombinants for Changes in Virulence Properties

Once the RPμhr23 recombinants containing the DNA fragments of interest have been constructed and isolated, changes in virulence resulting from the inserted DNA fragment can be ascertained. A two-component assay system has been developed to detect changes in virulence and tissue tropism. The first component involves the testing of the recombinant virus for changes in growth characteristics on a number of marker tissue culture cell lines in vitro. The cell lines selected have been shown to be predictive of certain growth characteristics within the animal. The second assay involves in vivo testing of the recombinants in the mouse for changes in $LD_{50}$ (death) or for causing sickness (i.e., weight loss). Here is described the application of these tests. The number of cell lines employed can be modified, and the use of substitute cell lines with similar properties is possible. Also, while we describe only one route of inoculation (intracranial—i.c.) of the virus into the mice, other routes (e.g., intraperitoneal—i.p.) may be used as well. The assay criteria for sickness is herein described; however, other indicators, such as elevated body temperature, can also be used. These two virulence assays can be used individually or in combination.

1. Assay for changes in host range in marker cell lines in vitro

Sufficient quantities of virus for testing are grown up on chicken embryo fibroblasts (CEFs) by standard procedures (and as described above). Changes in growth on the marker cell lines are determined by plaquing various dilutions of the virus on a panel of cell lines which we have shown to discriminate between various levels of virulence in the animal. These cell lines represent continuous lines of cells of different tissue and species origin. In a representative form of the assay, dilutions of the virus ranging from 1 to 10,000 pfu (as determined on the permissive avian cell lines) are added to confluent monolayers of the test lines in 60 mm dishes. The virus is allowed to adsorb for two hours, and then the monolayers are overlayed with 5 ml of semi-solid medium, typically 1×medium that contains either 0.75% agarose or 1% methylcellulose. The monolayers are then incubated for three days, at which time they are assayed by the addition of a vital dye, such as neutral red. The recombinants are evaluated either for the ability to form plaques as evidence of productive infection, or by changes in the cytopathic effects of the virus at the higher multiplicities of infection. The assay is performed with appropriate control viruses, such as RPμhr23 (which can grow only on the avian marker cell lines and which is avirulent in the mouse) and several other mutants with deletions of differing size which retain the ability to grow on one or more additional cell lines and which, in turn, show different virulence characteristics in the mouse. It is then possible to predict changes in the virulence properties of a given newly generated recombinant. This assay can be modified using substitute cell lines. Rather than a plaque assay, an end-point dilution type assay in a microtiter dish could be an appropriate substitute. An endpoint dilution assay could be monitored simply by changes in growth characteristics of the monolayer or by a ELISA reader.

2. Assay for changes in vivo using a sensitive weight loss model in the mouse

Since the properties governing virulence are complex, it is possible that a recombinant may not cause an increase in host range in cell culture, but be capable of causing sickness or death when administered to animals. The following assay is a sensitive complementary method to the in vitro assay discussed above for evaluating a recombinant for the ability to cause death or sickness. Here we describe an assay based on a weight loss model as an objective and sensitive assessment of sickness resulting from changes in virulence. The particular example cited results from insertion of a single fragment of DNA into the tester strain RPμhr23.

Sufficient quantities of the virus are grown up for testing as described above. Virus was purified for injection into mice essentially as follows: Typically infected cells from 10–150 mm dishes that had been infected at m.o.i. of 0.05–0.1 and harvested after 4 days at 37° C. were collected and resuspended in 10 ml of PBS. The virus was released from the cell debris by two rounds of freeze-thawing, followed by sonication for 30 seconds to one minute in a water bath sonicator. This mixture was then overlayed on a 5 ml 50% sucrose cushion in a Beckman SW27 tube, and brought up to volume (approx. 38 ml) in PBS. The virus was pelleted at 58,000 xg at 4° C. for 90 minutes. The supernatant was aspirated and the pellet drained and resuspended in 1.5 ml of PBS. The virus was resuspended using a chilled water bath sonicator, and layered onto a 36 ml linear 20–50% potassium tartrate gradient. Following centrifugation, for 60 minutes at 58,000 xg, the viral band was collected and diluted in PBS (at least 3 volumes). The virus was then pelleted through centrifugation at 90 minutes at 79,000 xg at 4° C., and resuspended in 500 μl-1 ml of PBS by sonication and repeated pipetting. This stock was titered and used neat or diluted in PBS for injection into mice.

Figure 5A:
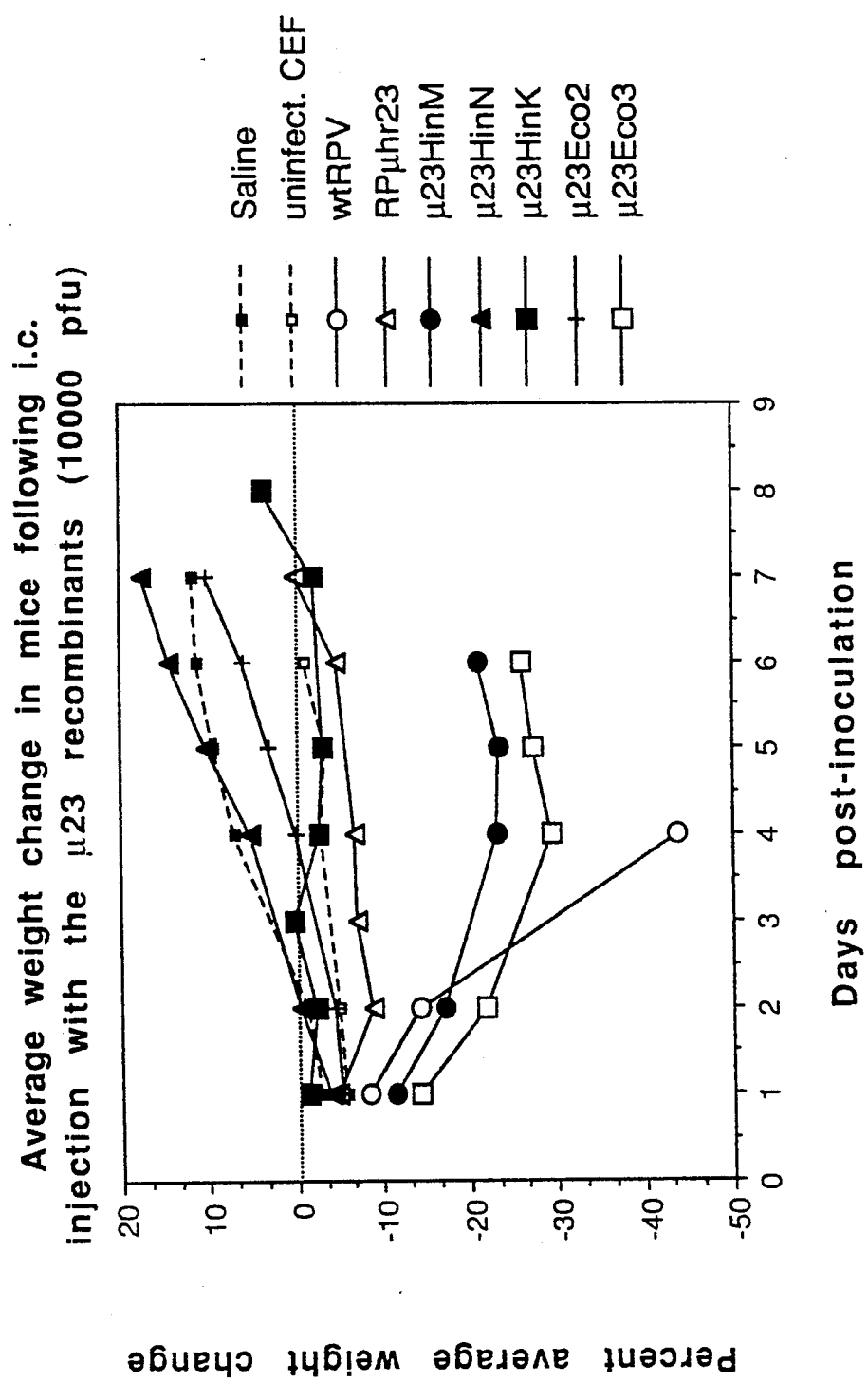
FIG. 5A shows average weight loss in mice following i.c. injection of mice with $1 \times 10^5$ pfu of the control tester strain alone (RP$\mu$hr23), wild type virus, and recombinants containing DNA inserted into the hemagglutinin gene of the tester strain by procedures as disclosed herein. Shown are recombinants containing fragments of the wild-type rabbit poxvirus genome missing in the tester strain but replaced in the recombinants that are being evaluated for their contributions to virulence. Controls include wild type RPV as well as mock infected CEF purified protein and saline. As can be seen, two of the recombinants (designated $\mu$23HinM and $\mu$23Eco3) cause significant weight loss, which is measured at day 4 post inoculation. One of these recombinants, $\mu$23Eco3, restores enough virulence to cause death in the mice, with an $LD_{50}$ of $2 \times 10^6$ pfu. In both cases, the mice show signs of clinical sickness, the magnitude of which corresponds with the relative weight loss. The $LD_{50}$ of RP$\mu$hr 23 is $> 1 \times 10^8$ pfu. The tester strain, RP$\mu$23, as well as several of the other recombinants ($\mu$23HinN, $\mu$23HinK, and $\mu$23Eco2) do not show clinical signs of sickness or weight loss. This shows the sensitivity of this model in detecting even small contributions to virulence by a piece of insert DNA encoding even a single gene, as in the case of $\mu$23HinM.
Figure 5B:
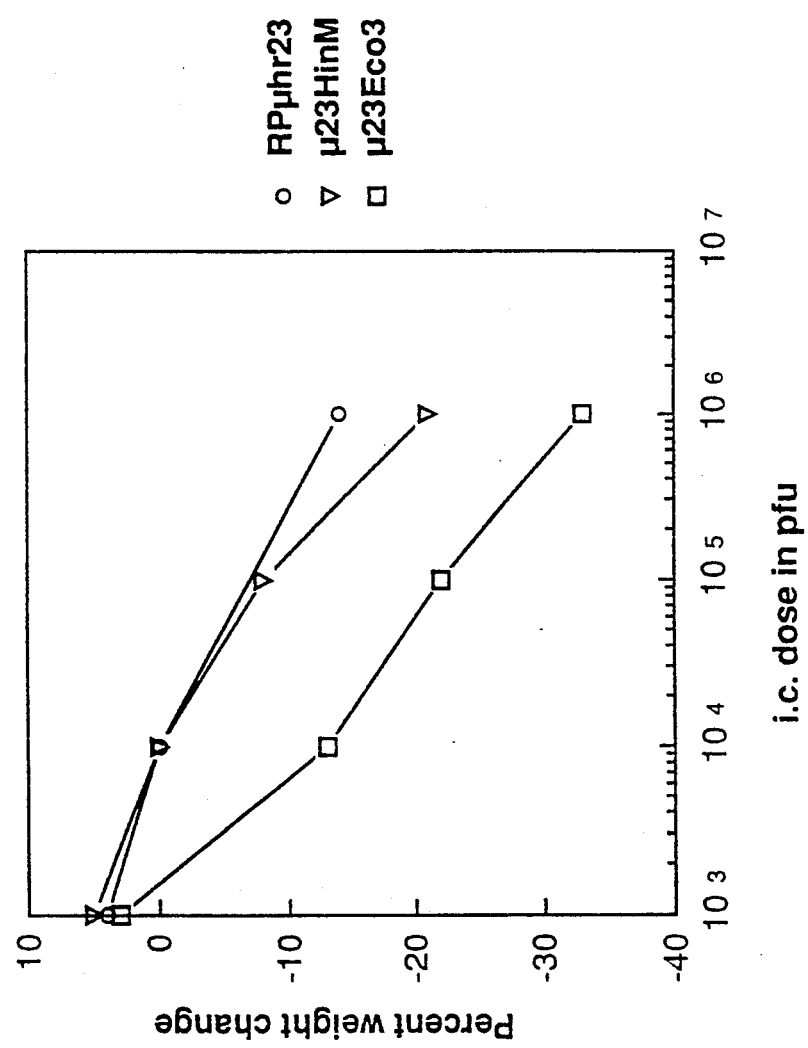
FIG. 5B shows dose dependent weight response (percent weight change) of the tester strain (RP$\mu$hr23) and two of the recombinants which demonstrate increased virulence ($\mu$23HinM and $\mu$23Eco3). The relationship of percent weight loss of each virus strain with change of dose demonstrates the sensitivity of the weight loss model in detecting even small changes in virulence.

Four to six week-old female BaLB/c mice (Sasco's pathogen-free colony) were maintained five to six mice per cage in an isolation unit. For intracerebral (i.c.) inoculations, virus (undiluted and diluted in PBS) was injected into the left cerebral hemisphere using a 27 gauge tuberculin syringe. Typical ranges of inoculum are from 20 pfu to $1\times10^7$ pfu. The mice were weighed just prior to injection and on each day thereafter. The mice were also watched closely for signs of illness and death. Weight loss was monitored for at least 6 days or until mice show either a positive weight gain for two or more subsequent days or until death. The $LD_{50}$ was determined by standard procedures. FIGS. 5A and 5B illustrate the sensitivity of this assay.

As can be seen, while RPμhr23 causes no change in virulence in the animal, several of the recombinants cause a significant amount of weight loss (up to 48% of the original body weight). Significantly, we have shown that this weight loss correlates with lethality, and that the weight loss is a much more sensitive assay for virulence than is $LD_{50}$ alone. Also significant is that the weight loss in several of the recombinants occurs prior to any predicted increase in virulence as measured by our in vitro cell culture assay. Therefore, we feel that the weight loss model is a sensitive assay that complements, but does not necessarily replace, the cell culture system as a means by which to evaluate contributions to virulence of a single gene or groups of genes.

Biological materials which can be used according to the subject invention have been deposited in the permanent collection of the American Type Culture Collection (ATCC), 12301 Parklawn Drive, Rockville, Md. 20852 USA. The accession numbers and deposit dates are as follows:

| Culture | Repository No. | Deposit Date |
|---|---|---|
| *Escherichia coli* pHGN3 | 69051 | August 17, 1992 |
| Rabbitpox virus RPμhr23HA+ | VR 2379 | August 13, 1992 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

We claim:

1. A biologically pure culture of a rabbit poxvirus denoted RPμhr23 HA+.

2. Plasmid pHGN3.

* * * * *